United States Patent [19]

Mullins et al.

[11] Patent Number: 6,086,864
[45] Date of Patent: *Jul. 11, 2000

[54] PHARMACEUTICAL FORMULATIONS COMPRISING POLYTHIOUREA AND METHODS OF USE THEREOF

[75] Inventors: Michael J. Mullins; William A. Fordyce, both of Midland; William J. Kruper, Sanford, all of Mich.; Norton P. Peet; Alan D. Cardin, both of Cincinnati, Ohio

[73] Assignees: Merrell Pharmaceuticals Inc., Midland, Mich.; The Dow Chemical Co., Bridgewater, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/979,031

[22] Filed: Nov. 26, 1997

Related U.S. Application Data

[63] Continuation of application No. 08/176,586, Jan. 3, 1994, abandoned.

[51] Int. Cl.[7] .......................... A61K 31/795; A61P 31/18; C08G 18/00
[52] U.S. Cl. ........................................... 424/78.37; 528/64
[58] Field of Search ..................... 528/52, 64; 424/78.37

[56] References Cited

U.S. PATENT DOCUMENTS

| | | | |
|---|---|---|---|
| 2,833,744 | 5/1958 | Neher | 260/77.5 |
| 2,868,834 | 1/1959 | Neher et al. | 260/506 |
| 3,528,949 | 9/1970 | Rutledge | 260/77.5 |
| 4,073,768 | 2/1978 | Mark | 260/45.75 |
| 4,328,244 | 5/1982 | Daniel et al. | 424/304 |
| 4,349,568 | 9/1982 | Markey et al. | 424/330 |
| 4,435,394 | 3/1984 | Ogata et al. | 424/248.5 |
| 4,471,110 | 9/1984 | Christell | 528/337 |
| 4,604,404 | 8/1986 | Munson et al. | 514/494 |
| 4,783,446 | 11/1988 | Neushul | 514/54 |
| 4,824,916 | 4/1989 | Kershner | 525/420 |
| 4,895,660 | 1/1990 | Kershner et al. | 210/640 |
| 4,966,894 | 10/1990 | Herr et al. | 514/56 |
| 5,124,149 | 6/1992 | Shapiro et al. | 424/93 T |
| 5,276,182 | 1/1994 | Cardin et al. | 564/49 |

FOREIGN PATENT DOCUMENTS

| | | |
|---|---|---|
| 544868 | 7/1954 | Belgium . |
| 0232744 | 8/1987 | European Pat. Off. . |
| 0498095 | 2/1991 | European Pat. Off. . |
| 0467185 | 1/1992 | European Pat. Off. . |
| 2669535 | 5/1995 | France . |
| 900094 | 10/1990 | South Africa . |
| 781479 | 8/1957 | United Kingdom . |
| 907829 | 10/1962 | United Kingdom . |
| 8800828 | 2/1988 | WIPO . |
| 9200749 | 1/1992 | WIPO . |
| 9314146 | 7/1993 | WIPO . |
| 9316992 | 9/1993 | WIPO . |

OTHER PUBLICATIONS

Antiviral Research, 18 (1992), "Sulfonic Acid Polymers as a New Class of Human Immunodeficiency Virus Inhibitors", Prem Mohan, et al., pp. 139–150.

R.M. Ottenbrite, ACS Symposium Series #186, pp 205–220 (1982) "The Antitumor and Antiviral Effects of Polycarboxyl–ic Acid Polymers".

G. Odian, Principles of Polymerization, 2d, p. 20–25 (1981).

Ahmed, et al., Antiviral Chemistry & Chemotherapy, (1995) 6(1), 34–42, "Potent Inhibition of Herpes Simplex Virus by MDL101028 a Novel Biphenyl Disulphonic Acid Co–polymer".

Cardin et al., "Stilbene Disulfonic Acids. CD4 Antagonists that Block human immunodeficiency Virus Type–1 Growth at Multiple Stages of the Viral Like Cycle" J. Biol. Chem (1991), 266(20), 13355–63.

Taylor et al, Potent Inhibition of Human Immunodeficiency Virus (HIV) by MDL 101028, a Novel Supphonic Acid Polymer.

Morgan, P.W., "Condensation Polymers: By Interfacial and Solution Methods", Title page Chap.4 (1965).

Berge et al., J Pharm. Sciences 66 (1), p. 1–19.

Komp et al, Chemical Abstracts vol. 110 Abstract No. 33727k (1989).

*Primary Examiner*—Edward J. Webman
*Attorney, Agent, or Firm*—Eric K. Voelk

[57] ABSTRACT

The oligomers of the present invention are polythioureas having 3 to 50 recurring units derived from aromatic diamines substituted with anionic groups, and having a number average molecular weight of less than 10,000. These oligomers are water-soluble, preferably have a rigid backbone, and are pharmaceutically-acceptable. The oligomers are useful for the treatment and/or diagnosis of AIDS.

5 Claims, No Drawings

PHARMACEUTICAL FORMULATIONS COMPRISING POLYTHIOUREA AND METHODS OF USE THEREOF

CROSS-REFERENCE TO RELATED APPLICATION

This is a continuation of application Ser. No. 08/176,586, filed Jan. 3, 1994 now abandoned, which is herein incorporated by reference.

This invention concerns pharmaceutical formulations comprising polythiourea oligomers and a method of use thereof. The polythiourea oligomers are anionic compounds that have particularly valuable anti-human immunodeficiency virus activity and these oligomers are thus useful in the treatment of acquired immune deficiency syndrome (AIDS)

BACKGROUND OF THE INVENTION

A great deal of research is currently underway to develop treatments and cures for viral infections in humans and in animals. Notably the incidence of AIDS and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including *Kaposi's sarcoma* and *Pneumocystis carninii pneumonia*. No cure for AIDS is known and current treatments are largely without adequate proof of efficacy and have numerous untoward side effects. Fear of the disease has resulted in social ostracism of and discrimination against those having or suspected of having the disease.

It has been disclosed in South African Patent 90/0094, issued Oct. 31, 1990, that a purified form of heparin, a sulfated polysaccharide, binds through interactions to a viral protein which is responsible for cell recognition and provides limited inhibition of host cell infection. However, heparin causes some side effects, notably hemorrhage and increased clot formation time as well as thrombocytopenia. Use of heparin is contraindicated in patients who are actively bleeding, or have hemophilia, purpura, thrombocytopenia, intracranial hemorrhage, bacterial endocarditis, active tuberculosis, increased capillary permeability, ulcerative lesions of the gastrointestinal tract, severe hypertension, threatened abortion or visceral carcinoma. The contraindication for use by hemophiliacs is particularly of concern because many such individuals are now HIV positive.

It has long been recognized that certain synthetic, water-soluble polymers exhibit a broad spectrum of biological activity [R. M. Ottenbrite in "Biological Activities of Polymers", *Amer. Chem. Soc. Symp. Ser.*, No. 182, pp. 205–220, eds. C. E. Carraher and C. G. Gebelein (1982)]. Although the mechanism of action of such water-soluble polymers is unknown, one postulate is that the polymer binds to the viral membrane through an ionic attraction, thus rendering the virus unable to infect host cells. Unfortunately, the extreme toxicity of these polymers has prevented their clinical use. Also, these polymers have a high molecular weight and are unable to pass through the renal membranes.

Attempts have been made to circumvent the toxicity and excretion problems by synthesis of low molecular weight (1,000 to 10,000) aliphatic polymers [R. M. Ottenbrite in "Biological Activities of Polymers", *Amer. Chem. Soc. Symp. Ser.*, No. 182, pp. 205–220, eds. C. E. Carraher and C. G. Gebelein (1982)]. It has been found that such polymers are less toxic but have much reduced anti-viral activity. These low molecular weight aliphatic polymers may be classed as "random coil" polymers. Such polymers have an unpredictable configuration because of the flexibility of the backbone linking groups. The configuration of random coil polymers in solution may be generally described as globular. The reduced anti-viral activity of these random-coil polymers is believed to be due to a low binding affinity of the polymers with the viral membrane.

One approach to overcome the problems with the random-coil polymers would be to provide polymers which have rigid backbones with few degrees of freedom.

Certain chiral anionic oligomers which inhibit viral replication without the side effects shown by heparin and known polymers have now been found. These anionic oligomers have ordered anionic spacing, have a rigid backbone and are water-soluble. The anionic oligomers, as polydispersed mixtures, have been described in our copending U.S. patent application Ser. No. 710,370, filed Jun. 10, 1991, and corresponding PCT Application Serial No. PCT/US91/04804, filed Jul. 8, 1991, the disclosures of which are incorporated herein by reference. The anionic oligomers, as narrow poly- and mono-dispersed oligomers, have been described in U.S. patent application Ser. No. 818,753, filed Jan. 9, 1992, the disclosure of which is incorporated herein by reference.

Certain achiral anionic polyurea oligomers with rigid backbones and having few degrees of freedom have been described in a concurrently filed application.

Certain polythioureas have been disclosed for their anti-viral activity in Belgian Patent No. 544,868, issued Jul. 31, 1956.

SUMMARY OF THE INVENTION

It has now been discovered that certain polythiourea oligomers possess anti-human immunodeficiency virus activity and are thus useful in the treatment of AIDS, and ARC. The oligomers include their pharmaceutically-acceptable salts.

The present invention, therefore, relates to water-soluble, rigid backbone, polythiourea oligomer comprising recurring moieties derived from a compound represented by the Formula:

$$H_2N-X-NH_2 \qquad (I)$$

wherein X is a divalent aromatic hydrocarbylene radical substituted with at least one sulfonic acid group.

The oligomers of the invention possess ordered anionic spacing between the anionic sulfonic acid groups. The number average molecular weight $M_n$ of the oligomers is less than 10,000.

DETAILED DESCRIPTION OF THE INVENTION

The oligomers of the invention are represented by the Formula:

(II)

wherein R is a hydrogen, a $C_1$–$C_4$ alkyl, a phenyl, or a phenyl substituted with from 0 to 2 $R^1$ groups and up to 3 substituents independently selected from a chloro or a bromo atom, or a $C_1$–$C_4$ alkyl group; $R^1$ represents —$SO_3R^2$, —$CO_2R^2$, —$PO_3R^2$, or —$OPO_3R^2$; $R^2$ is a hydrogen or a pharmaceutically-acceptable cation; $R^3$ is —R or —X—NHR, where in R is as defined above; X represents Y represents —$CO_2$—, —C≡C—, —N=N—, m is an integer 0 or 1, with the proviso that when m is 0, R is a hydrogen atom, and n is an integer from 3 to 50 and with the proviso that at least one of $R^1$ in the definition of X is —$SO_3R^2$.

Preferred terms for Formula I are as follows:

R and $R^3$ are 4-methylphenyl group;

m is 1;

n is 3 to 15; and

X represents

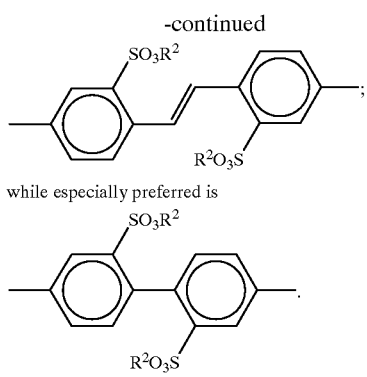

while especially preferred is

The term "pharmaceutically-acceptable cation" means a cation acceptable for pharmaceutical use. Those cations that are not substantially toxic at the dosage administered to achieve the desired effect and do not independently possess significant pharmacological activity are included within the term "pharmaceutically-acceptable cation". Illustratively, these salts include those of alkali metals, such as sodium and potassium; alkaline earth metals, such as calcium and magnesium; ammonium; light metals of Group IIIA, including aluminum; and organic primary, secondary and tertiary amines, such as trialkylamines, including triethylamine, procaine, dibenzylamine, N,N'-dibenzylethylendiamine, dihydroabietylamine, N-($C_1$–$C_4$) alkylpiperidine, and any other suitable amine. Sodium and potassium salts are preferred.

The term "pharmaceutically-acceptable" means suitable for administration to warm-blooded animals, especially human beings, and includes being nontoxic, e.g., suitable for pharmaceutical use and is not poisonous to the warm-blooded animal. The pharmaceutically-acceptable cations of the oligomers of the present invention are prepared by conventional ion exchange processes or by treating the $R^1$ acid with an appropriate base.

When uses other than for pharmaceuticals are the object for the present oligomers, then salts that would otherwise not be as acceptable for pharmaceutical uses may be employed. Examples of such additional salts include barium, zinc and titanium.

By "ordered spacing" or "regular spacing between anionic groups" is meant that the anionic sulfonic acid groups are present in the backbone of the polymer at intervals determined by the starting material reagent used and the occurrence of the anionic groups is controlled in a predictable manner. While not wishing to be bound by any theory, the sulfonic acid groups of the oligomers are believed to be the portion that binds to the HIV and/or cell membrane and thereby interrupts the ability of the virus to replicate.

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but able to inhibit the HIV virus. The average molecular weight is governed by the stoichiometry of the reagents. The number average molecular weight ($M_n$) is <10,000, preferably from about 500 to about 10,000, and most preferably from about 1,000 to about 6,000.

For the purpose of the present invention, the oligomers described herein and physiologically-acceptable salts thereof are considered equivalent. Physiologically-acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like; and ammonia, primary, secondary and tertiary amines and the like. Particularly preferred bases are the alkali metal hydroxides, carbonates, and bicarbonates. Physiologically-acceptable salts may be prepared by conventional ion exchange processes or by treating the $R^1$ acid with an appropriate base. Examples of additional salts have been described herein.

The formulations of the present invention are in the solid or liquid form. These formulations may be in kit form such that the components are mixed at the appropriate time prior to use. Whether premixed or as a kit, the formulations usually require a pharmaceutically-acceptable carrier or adjuvant.

The oligomers of the present invention are soluble in water and in salt solutions, especially at physiological pH and in saline solutions. Thus the present oligomers are readily formulated into a suitable aqueous pharmaceutical dosage form. Also, after the present oligomer formulation is administered, the oligomer remains soluble in vivo.

Oligomers in solution as ammonium salts of volatile amines can be converted to more preferred pharmaceutically-acceptable salts, such as the sodium or potassium salts, by treating the solution with an alkali metal salt of a weak volatile acid. Upon concentrating the solution by evaporation or lypholization, the amine and weak acid are removed and the oligomers are isolated as their alkali metal salts. Suitable examples of ammonium salts which may be converted in the step are salts of ammonia, monoethylamine, triethylamine, trimethylamine or dimethylamine (herein to as "ammonium salts"). Examples of alkali metal salts are sodium or potassium hydroxide, bicarbonate, acetate, formate or propionate.

PREPARATION OF THE ANIONIC OLIGOMER

The anionic polymers are prepared using two methods. The first process, a non-specific method which produces a polydisperse mixture of oligomers, involves combining a diamine with a thiourea precursor, such as thiophosgene or thiocarbonyl diimidazole. Optionally present are a monofunctional end-capping agent, an acid acceptor to control the reaction pH, and a water-immiscible solvent. A process is also described for conversion of a non-capped polythiourea with amine ends to the capped polymer using a monofunctional amine-reactive agent, or by combining the uncapped polymer with an amine-containing monofunctional end-capping agent and a thiourea precursor.

The second method involves a stepwise build-up of the polymer chain by successive addition of a bisisothiocyanate and a diamine. Although this method is more tedious, a polythiourea with narrow dispersity is produced.

The process for the preparation of the polythioureas is further explained as follows.

Diamines: The diamines of the present invention are primarily aromatic, with the formulas described in previous sections. Such diamines are substituted with at least one group which is charged at neutral pH, preferable sulfonate. Monovalent aliphatic substituents are allowable. A small set of aliphatic linking groups which tie aromatic radicals together may be used such as trans-substituted ethylene and acetylene. Preferred diamines are those in which the carbon-nitrogen bonds are forced to be parallel, such as 2,5-diamino-1,4-benzenedisulfonic acid, 4,4'-diamino-(1,1'-biphenyl)-2,2'disulfonic acid, trans-2,2'-(1,2-ethenediyl)bis (5-aminobenzenesulfonic acid) and 2,5-diaminobenzensulfonic acid.

Thiourea precursors: A variety of thiourea precursors or difunctional electrophile such as thiophosgene (thiocarbonyl dichloride), thiocarbonyl dibromide, and other urea precursors such as thiocarbonyl diimidazole, hexachlorothioacetone, $Cl_3CSCO_2CCl_3$, $CCl_3CSCl$, and $Cl_3OCSCl$ may be used.

Acid Acceptors: A variety of inorganic bases may be used, such as alkali metal or divalent metal hydroxides carbonates, bicarbonates, phosphates. Acid acceptors with buffering capacity are preferred when all of the base is added prior to the addition of the difunctional electrophile. Organic bases such as trialkyl amines may be used, but are not preferred.

Monofunctional end capping agent: A variety of such molecular weight limiting agents may be used. Such agents may be aliphatic or aromatic compounds which react with the diamines or the difunctional electrophiles. Examples of suitable monofunctional agents are amines such as aniline, methylaniline, methylamine, ethylamine, butylamine, diethylamine, ammonia and N-methylaniline. Examples of monofunctional amine reactive agents are benzoyl chloride, methyl benzoyl chloride, acetyl chloride, methyl isocyanate, methyl isothiocyanate, phenyl isocyanate, phenyl isothiocyanate, p-tolyl isothiocyanate and phenyl chloroformate. These end-capping agents may also contain charged substituents, for example potassium 2-sulfophenol or potassium 4-sulfoaniline.

Miscellaneous additives: The addition of surfactants is not necessary or preferred, and can complicate the isolation process.

Solvents: A single solvent, water, is preferred when the difunctional electrophile is a liquid at the reaction temperature. An example of such a difunctional electrophile is thiophosgene. When solid, water insoluble reactants are used, a small amount of a water immiscible cosolvent is desirable. Example of such water immiscible cosolvents are chloroform, carbon tetrachloride, toluene, and methylene chloride. Typical ratios of organic to aqueous solvents are 0 to 1, with 0 to 0.1 preferred.

The process is conducted at temperatures which allow the reaction to proceed, typically from about 0 to 100° C. Preferable temperatures are 0 to 25° C. When thiophosgene is used, good mixing is important. Small lab-scale experiments were conducted in a Mixxor™, a simple glass device operated by hand, in which the reactants are forced back and forth through a narrow channel. The pressure is not important and typically ambient pressure is employed. The pH of the reaction must be carefully maintained for optimum process. One consideration is that the charged diamines have limited solubility at acidic pH values of less than 4. Also, at low pH (<6) the reaction is very slow, while at high pH (>10) the difunctional electrophile is unstable to attack by hydroxide or other base. Degradation of the polythiourea can also occur at high pH. The pH is preferably maintained between 6 and 9.

When no end-capping agent is used, molecular weight control can be achieved by careful adjustment of the stoichiometry of the reactants or by using the second process. Either the diamine or the difunctional electrophile may be used in excess, for example from 1 to 100 percent molar excess. This stoichiometry must account for any of the difunctional electrophile which is destroyed by hydrolysis prior to reaction with the diamine. For example, when thiophosgene is used at high pH, a large excess is required to compensate for the fast reaction with hydroxide which destroys it. Because the extent of this side reaction is difficult to control, a monofunctional end-capping agent is preferably used to control the molecular weight. Although the techniques mentioned can be used to control the number average molecular weight when the first process is used, the products are mixtures of polymers with several molecular weights characterized by a distribution.

The order of addition of the reactants is not critical. However, the preferred order is to add the difunctional electrophile first. When acid acceptors which are not buffers are used, such as hydroxide, it is most preferable to add a portion at the beginning to achieve the desired pH, and then add the remainder concurrently with the difunctional electrophile.

The concentration is not critical, and may be from 0.5 to 50 weight percent, expressed as weight of diamine to weight of solvent. A preferred range is 0.5 to 5 weight percent.

The second process, designed to produce polythioureas with narrow dispersity, is shown below. In this process the chain length is increased by two repeat units each time the two-step cycle is repeated. To illustrate, consider the case where the starting material is a simple diamine ('n'=0 in top formula). The diamine is converted with a thiourea precursor, such as thiophosgene, to a bis-isothiocyanate (middle formula with 'n'=0). Treatment of the bis-isothiocyanate with an excess of the diamine gives the thiourea oligomer with 2 repeat units ('n'=2 in bottom formula). This sequence is repeated to build chain length in the sequence 0, 2, 4, 6, and so on.

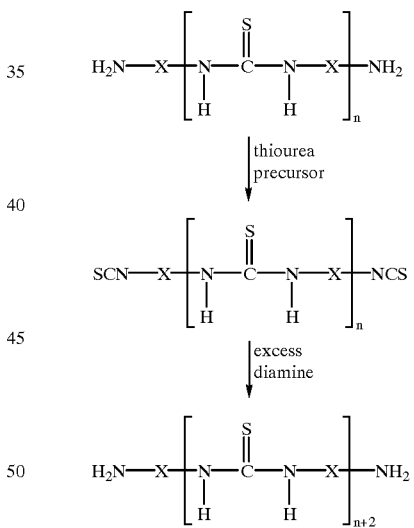

In this process the conditions for each step are similar to those described above for the first process in which a polydisperse polythiourea are produced. The primary difference is that the stoichiometry of the reactants in the previous method was nearly 1:1. In this process the added reagent, the thiourea in the first step, and the diamine in the second step, are added in large excess. The molar ratio of growing chain to added reagent is roughly 1:3 to 1:50, with the preferred range being 1:5 to 1:10.

There is no need to isolate the growing chain at any stage. A preferred method is to treat the diamine (or oligomer with amine ends) with an excess of the thiourea precursor for sufficient time to completely convert the amine ends to isothiocyanates. The excess thiourea precursor is then removed by extraction into a water-immiscible solvent such as methylene chloride. The aqueous solution of the bis-isothiocyanate is then treated with excess diamine. It is possible, however, to isolate the bis-isothiocyanate as was done in one case described in the examples.

The product may be isolated by precipitation of the reaction solution into a solvent which is water miscible but is a poor solvent for the product. Examples of such solvents are acetone, methanol, ethanol, isopropanol.

FORMULATIONS AND METHOD OF USE

Anti-HIV anionic oligomers can be used to prevent syncytium formation in cells infected with HIV-I virus or other related viruses having gp120 surface protein. Anti-HIV anionic oligomers can be used to treat AIDS and ARC and other diseases caused by the retrovirus HIV-I or other related viruses having gp120 surface protein.

The amount of anti-HIV anionic oligomers which is needed to prevent syncytium formation in HIV infected cells can be any effective amount. Experimentally, it has been determined that anti-HIV anionic oligomers, when employed at a concentration of 10 $\mu$g/mL of aqueous formulation, resulted in complete inhibition of syncytium formation as well as reduced the presence of p24 antigen, an indicator of viral replication, to below 300 pg/ml. The amount of anti-HIV anionic oligomers to be administered in order to treat AIDS or ARC or other disease caused by HIV infection can vary widely according to the particular dosage unit employed, the period of treatment, the age and sex of the patient treated, the nature and extent of the disorder treated, and other factors well-known to those practicing the medical arts. Moreover anti-HIV oligomers can be used in conjunction with other agents known to be useful in the treatment of retroviral diseases and agents known to be useful to treat the symptoms of and complications associated with diseases and conditions caused by retroviruses.

The anti-HIV effective amount of anti-HIV anionic oligomers to be administered according to the present invention will generally range from about 0.1 mg/kg to 500 mg/kg of body weight of the patient and can be administered one or more times per day.

Anti-HIV anionic oligomers can be administered with a pharmaceutical carrier using conventional dosage unit forms either orally or parenterally.

For oral administration, anti-HIV anionic oligomers can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, sorbitol, calcium phosphate, and cornstarch. In another embodiment the anionic oligomers of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene glycols, either with or without the addition of a pharmaceutically-acceptable surfactant, suspending agent, or emulsifying agent.

The anti-HIV anionic oligomers of this invention may also be administered parenterally, that is, sub-cutaneously, intravenously, intramuscularly, or inter-peritoneally, as injectable dosages of the anionic oligomers in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepoly-propylene copolymers; and amphoteric detergents, for example, alkyl-beta-aminopropionates, and 2-alkyl-imidazoline quarternary ammonium salts, as well as mixtures. The parenteral compositions of this invention will typically contain from about 0.5 to about 25 percent by weight of anti-HIV anionic oligomer in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15 percent by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate.

The anionic oligomers of this invention can also be used prophylactically, that is, to prevent transmission of virus from an infected individual to an uninfected target. Virus is spread proportionally via exchange of blood but may be transmitted via exchange of other bodily fluids as well. Thus, the oligomers of this invention can be formulated with standard detergent products for use in cleaning, particularly in research and clinical laboratories and in hospitals where blood products of infected individuals are handled. Formulations containing the oligomers of the present invention can be used to clean medical/surgical equipment and utensils as well as the hands of and other skin areas of health care workers. The oligomers of this invention can also be applied, as a liquid or powder composition, to the surface of sexual prophylactic devices such as condoms by either the user or manufacturer of the prophylactic devices prior to sale. The oligomers of this invention can be formulated into a douche composition for use by females for use prior to subsequent sexual contact with an infected individual. The oligomers of this invention can also be formulated in lubricants and spermacidal jellies and lotions. Finally, the oligomers of this invention can also be formulated as compositions to be added to hot tubs, whirlpool baths and swimming pools to inactivate potential virus activity.

The invention will be further clarified by a consideration of the following examples, which are intended to be purely exemplary of the present invention.

DEFINITIONS

The terms used in the present examples are defined as follows, unless stated otherwise, and for example represent an instance of suitable equipment or resins, but similar equipment or differing parameters or resins may be used:

TCID50=tissue culture infectious dose, i.e., the amount of culture fluid effective to infect 50 percent of the cells (50 percent cytopathic effect) at 7 days post infection;

MTT=tetraazolium reduction reagent;

3-(4,5-dimethylthiazol-2-yl)-2,5-diphenyltetrazolium bromide;

RPMI=a cell culture;

RF and GB8 mean HIV-I virus strains;

MT4, C8166 and JM=cell lines;

P24 test-Abbott means an assay of the viral core antigen using the assay kit currently sold by Abbott.

EXAMPLE 1A

Preparation of Polythiourea Using Specific Method
Preparation of Bis-Isothiocyanate

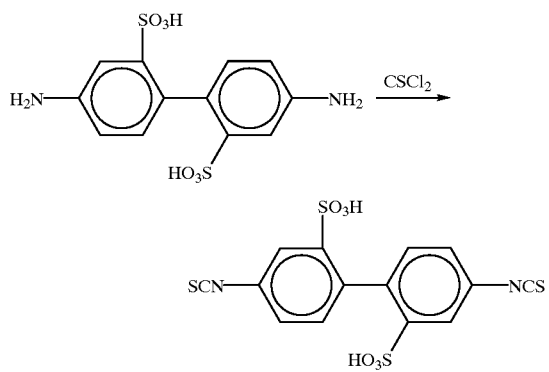

The 4,4'-diaminobiphenyl-2,2'-disulfonic acid (1.2 g, 3.48 mmole) was vigorously stirred with 15 mL water and 600 μL of thiophosgene for 3 hours. Additional thiophosgene was added (250 μL) was added, and the reaction was stirred for an additional 14 hours. The product was isolated by filtration through a medium porosity sintered glass filter funnel, yielding 70 mg of residual insoluble monomer. The clear, purple filtrate was evaporated at less than 50° C. at approximately 10 mmHg, dried in vacuo for 3 hours, yielding 1.35 g, 31.5 mmoles of bisisothiocyanate dihydrate as a pale lavender, deliquescent solid. The product was characterized by proton and carbon nuclear magnetic resonance as well as combustion analysis.

Preparation of Uncapped Polythiourea

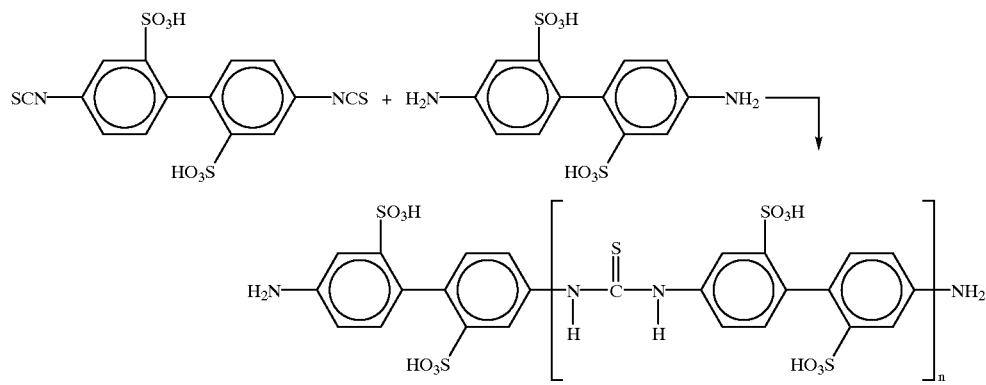

Excess 4,4'-diaminobiphenyl-2,2'-disulfonic acid (6.0 g, 46.5 mmole) was mixed with 2 equivalent of $NaHCO_3$ (8.2 g, 97.6 mmole), causing the pH to rise to 7.5. To this stirred solution was added a solution (30 mL) of the above-prepared bis-isothiocyanate (2.17 g, 4.67 mmole, pH 1.5) over a 10 minute period. After the addition was complete, the pH had dropped to 6.5 and the reaction was stirred for 14 hours. The pH was then adjusted to 1.8 with 12 M HCl, and after 8 hours the white solid which formed was filtered and washed with 25 mL of cold 0.1M HCl. The solid was vacuum dried to give 12.0 g of unreacted starting material (4,4'-diaminobiphenyl-2,2'-disulfonic acid) as white solid. The filtrate was evaporated, giving 10.0 g of a dark purple solid. This filtrate was identified spectroscopically as nearly pure polythiourea (II, n=0 contaminated with a small amount of starting diamine (4,4'-diaminobiphenyl-2,2'-disulfonic acid) and NaCl.

Purification of Uncapped Polythiourea

A gel filtration column was prepared by allowing 115 g of Pharmacia Sephadex® G-10 (40–120 μm bead size) resin to swell in approximately 500 mL of distilled water for 1 hour. Fines were decanted from the resin mixture after allowing the suspension to settle in a 1 L graduated cylinder. A glass column was slurry packed with the resin and 500 mL of distilled water was passed through the column resulting in a 2.5×50 cm bed. A constant flow rate was maintained through the column using a Gilson Minipuls peristaltic pump (flow rate approximately 3–4 mL per minute). The eluent was monitored at 310 nm (Isco model UA-5 ultraviolet detector for the presence of product.

A solution of 50 mg of the above-prepared polythiourea oligomer was dissolved in 2.5 mL of distilled water and carefully applied to the top of the column. The column was eluted with distilled water and three product fractions (15 mL each) were collected. Analysis of the fractions by HPLC indicated that the first fraction contained the polythiourea, which was free from starting diamine and salt.

EXAMPLE 1B

Preparation of Uncapped Polythiourea by Non-specific Method Using Thiophosgene

A sample of 4,4'-diaminobiphenyl-2,2'-disulfonic acid (100 mg, 0.29 mmole) was added to 50 mL water and approximately 4 mL 0.1M NaOH was slowly added to dissolve the solid. The pH of the solution rose to 6.8. This solution was added to a Mixxor™, a device which allows convenient vigorous mixing of immiscible liquids, and 2.21 mL (0.29 mmole of thiophosgene) of a stock solution of thiophosgene (100 μL) in 10 mL of chloroform was added. After 2 minutes of mixing the pH of the solution was adjusted to 6–7 by the addition approximately 2.5 mL of 0.1M NaOH. The solution was heated in a 45° C. oil bath for 16 hours, and the solvent was evaporated. Analysis of the resultant solid by HPLC indicated that a mixture of polythiourea oligomers was produced.

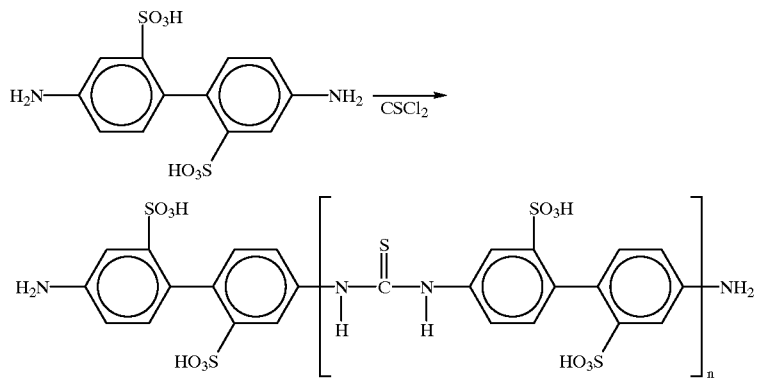

EXAMPLE 1C

Preparation of Uncapped Polythioureas Using Thiocarbonyl-Diimidazole

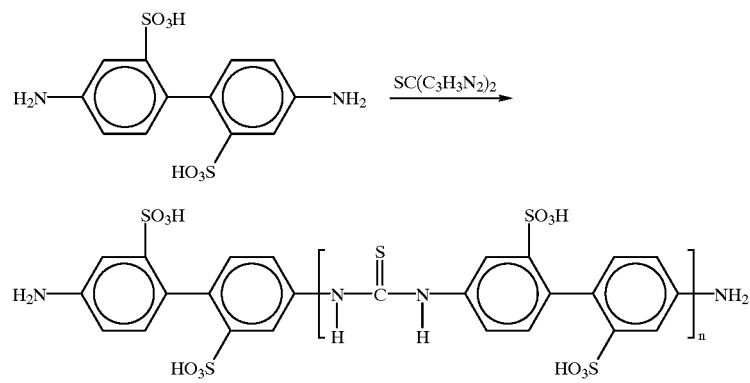

Recrystallized 4,4'-diaminobiphenyl-2,2'-disulfonic acid (1.00 g, 2.91 mmol) was added to 50 mL of water as slurry, followed by the addition of sodium bicarbonate (489 mg, 5.82 mmol.). The resultant of pH of 6.5 was reached upon dissolution of the solid. Thiocarbonyl diimidazole (600 mg, 3.37 mmol, Aldrich Chemical Co.) was added to the stirred solution with vigorous stirring with the development of a bright yellow color. Within five minutes, the color faded and the reaction was stirred for 24 hours. At this point the distribution of oligomers observed by HPLC did not change with time. The solvent was evaporated in vacuo (T=35° C.) to afford 1.8 g of crude thiourea oligomers which contained n=4 as the largest component by HPLC (n=4 at 9.9 area percent at 254 nm).

Preparation of Capped Polythiourea Oligomers From Uncapped Oligomers

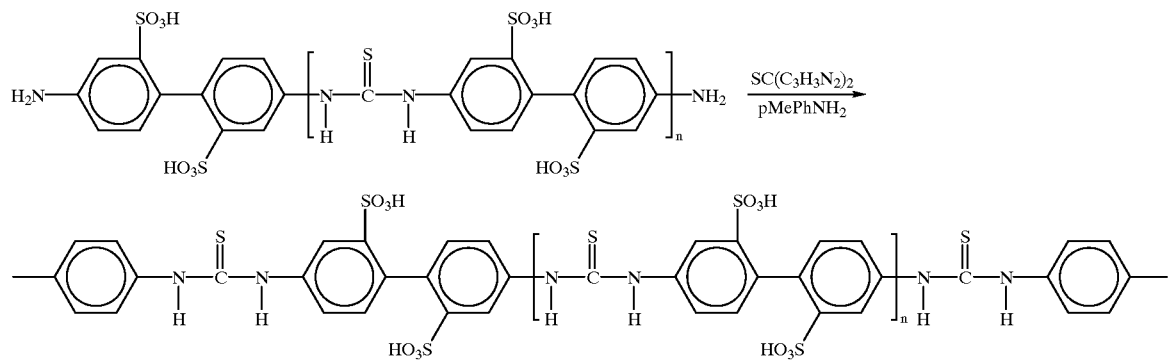

Uncapped polythiourea oligomer (400 mg) prepared as described above was dissolved in 15 mL of water. Five percent hydrochloric acid was used to adjust the pH to 4.5. Thiocarbonyldiimidazole (100 mg, Aldrich Chemical Co.) was added with stirring and a pH of 6.6 obtained after 15 minutes of stirring. HPLC analysis revealed the distribution of oligomers was changed to a series of more lipophilic species (terminal isothiocyanate). Toluidine (80 mg) was added with immediate formation of a white precipitate (toluidine thiourea). After stirring the slurry for 20 minutes (pH of 7.0), the solution was filtered and the mother liquor evaporated ($10^{-1}$ mm, 35°)to give 537 mg of p-toluidine capped polythiourea oligomers. HPLC analysis indicated to trace of the precursor isothiocyanate terminated species (the toluidine capped material is even more lipophilic and the series elutes at even longer retention times).

Fractionation of Uncapped Polythiourea Oligomers

The crude uncapped polythiourea prepared as described above (500 mg) was dissolved in 2 mL of water and the solution was applied to a 26 mm×90 cm $G^{-10}$ size exclusion gel column (Pharmacia). Fractions collected (20 mL) were analyzed by HPLC and the first two UV active fractions (254 nm) were estimated to contain n=7.2. These were combined and evaporated to give 140 mg of number average dispersity n=7.2 as determined by $^1H$ NMR analysis end group analysis. The structure were consistent with both the 13C and $^1H$ NMR analyses.

BIOLOGICAL DATA

EXAMPLE I

Ability of an Anti-HIV Oligomer to Prevent Syncytia Formation and Expression of P24 Viral Core Antigen Using JM Cells and GB8 Virus Strain To show that an oligomer of the invention blocks HIV infection, CD4+ T-cells (JM) were exposed to the GB8 strain of HIV-I, GB8. The virus was first incubated with an oligomer for 15 minutes and then the cells were added. After 2 hours adsorption, the virus innoculum was removed, the cells were washed three times to remove traces of input virus and the cells were incubated in the presence of the compound. Antiviral activity was determined after 3 days incubation by plotting the mean number of syncytia found in quadruple cultures against $\log_{10}$ concentration of anionic polymer or of other test compounds. The potency of an oligomer was also measured by assaying viral core antigen (P24 test-Abbott) in the supernatant fluid. Heparin, dextran sulfate, rs CD4, ATZ and/or ddC data, when included in any of the following Tables, are provided as positive controls.

The data are summarized in Table I

TABLE I

| Compound | $ED_{50}$ (μg/ml)+ |
|---|---|
| Example 1C uncapped | 1.9 |
| Example 1C capped | 0.46 |

+Effective dose yielding 50 percent inhibition of HIV-1 induced syncytia formation of JM cells by the GB8 viral strain

Ability of an Anti-HIV Oligomer to Prevent HIV-Induced Cell Death Using MT-4 Cells and the RF Virus Strain In this experiment, 1.5 ml of RPMI medial was added to each tube to dissolve the test compound. Compounds were then assayed for HIV-I activity by making doubling dilutions of the solutions across a microtitre plate. $5 \times 10^4$ cells and 100 $TCID_{50}$ units of virus were then added to each well and the plates incubated at 37° C. for 7 days. MTT was added to each well and the plates incubated for a further two hours. The blue formazan crystals were dissolved using acid isopropanol and the absorbence measured at 540 nm.

The data are illustrated in Table II below.

TABLE II

| Compound | ED$_{50}$ (μg/ml)+ | CD$_{50}$ (μg/ml)+ |
|---|---|---|
| Example 1C uncapped | 5.1 | ≧100 |
| Example 1C capped | 8.5 | ≧100 |

+Effective dose yielding 50 percent inhibition of HIV-1 induced cell death of MT-4 cells by the RF viral strain in the MTT assay.
*Cytotoxic dose of compound yielding 50 percent toxicity to MT-4 cells in the MTT assay.

Effect of Anti-HIV Oligomers on the Growth of HIV-I$_{RF}$ in the C8166 T Cell Line Protocol: C8166 cells were infected with HIV-I$_{RF}$ for one hour at room temperature. The cells were then washed twice in RPMI and distributed into wells of a tissue culture plate containing varying concentrations of test compound or no compound (control). After 3 days incubation at 37° C., the cells were observed for the presence of syncytia and the cell-free supernatant fluid was assayed for levels of P24 viral core antigen using an ELISA. The results are set forth in the Tables III and IV below.

TABLE III

| COMPOUND | CONC. μg/mL | SYNCYTIA | P24 (pg/mL) | % CONTROL |
|---|---|---|---|---|
| Example 1C uncapped | 100 | 0 | Negative | 0 |
| | 10 | + | 55950 | 14 |
| | 1 | ++ | 241460 | 59 |
| | 0.1 | +++ | 508610 | >100 |
| | 0.01 | +++ | 376670 | 93 |
| Example 1C capped | 100 | 0 | Negative | 0 |
| | 10 | 0 | Negative | 0 |
| | 1 | +/++ | 150668 | 37 |
| | 0.1 | ++ | 389080 | 96 |
| | 0.01 | +++ | 435450 | >100 |

TABLE V

| Compound | ED$_{50}$ (μg/ml)+ |
|---|---|
| Example 1C uncapped | 1.6 |
| Example 1C capped | 0.6 |

+Effective dose yielding 50 percent inhibition of HIV-1 induced syncytia and P24 viral antigen scores in C98166 cells infected with the RF viral strain.

What is claimed is:

1. A water-soluble, rigid backbone, polythiourea oligomer corresponding to the formula:

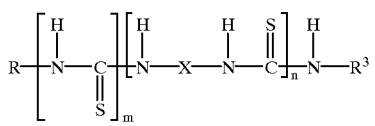

wherein

R is hydrogen, C$_1$–C$_4$ alkyl, phenyl or phenyl substituted with 0 to 2 R$^1$ groups and up to 3 substituents independently selected from chloro, bromo or C$_1$–C$_4$ alkyl;
R$^1$ represents —SO$_3$R$^2$, —CO$_2$R$^2$, —PO$_3$R$^2$ or —OPO$_3$R$^2$;
R$^2$ is hydrogen or a pharmaceutically acceptable cation;
R$^3$ is —R, where R is defined as above;

X represents

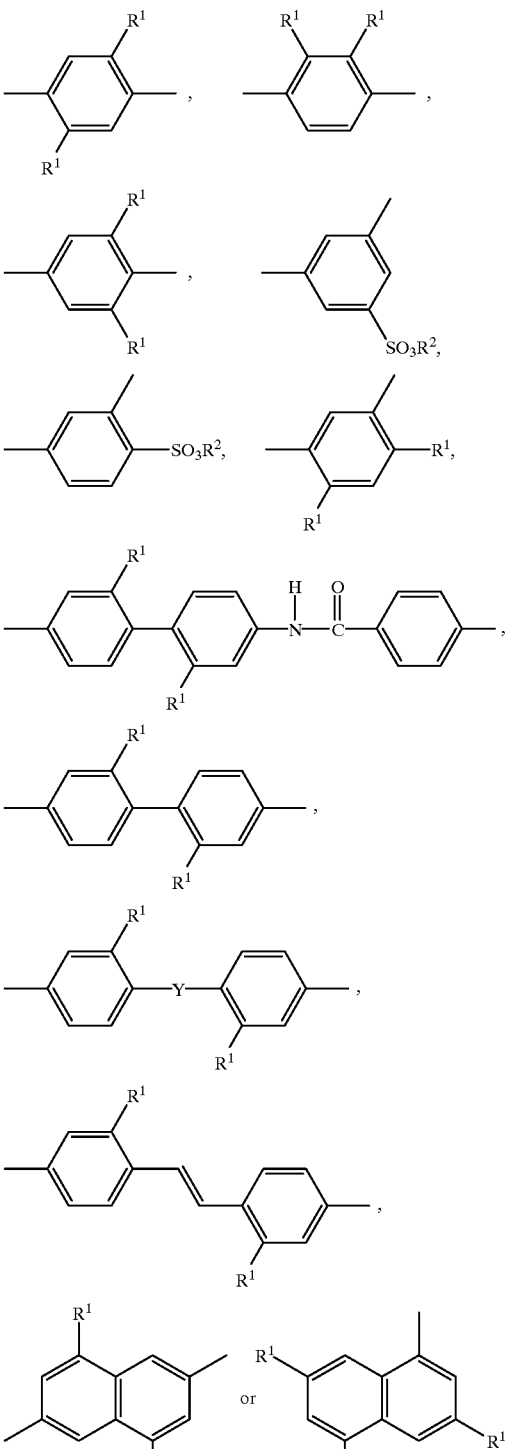

m is an integer 0 or 1;

n is an integer from 3–50;

with the proviso that when m is 0, both R and $R^3$ are not simultaneously hydrogen;

and with the additional proviso that at least one $R^1$ of X is —$SO_3R^2$.

2. The oligomer of claim 1, wherein the number average molecular weight is less than 10,000.

3. The oligomer of claim 1, wherein the oligomer is in the form of its salt.

4. The oligomer of claim 1, wherein R is hydrogen, m is 1, R and $R^3$ are 4-methylphenyl, n is 3 to 15 and X represents.

5. The oligomer of claim 1 wherein m is 1, R and $R^3$ are 4-methylphenyl, n is 3 to 15, and X represents.

* * * * *

UNITED STATES PATENT AND TRADEMARK OFFICE
CERTIFICATE OF CORRECTION

PATENT NO.   : 6,086,864
DATED        : July 11, 2000
INVENTOR(S)  : Michael J. Mullins, William A. Fordyce, William J. Kruper, Norton P. Peet and Alan D. Cardin It is certified that error appears in the above-identified patent and that said Letters Patent is hereby corrected as shown below:

Column 20,
Line 3, reads as "wherein R is hydrogen, m is 1," and should read as
-- wherein m is 1 --
Line 5, reads as "represents." and should read as -- represents

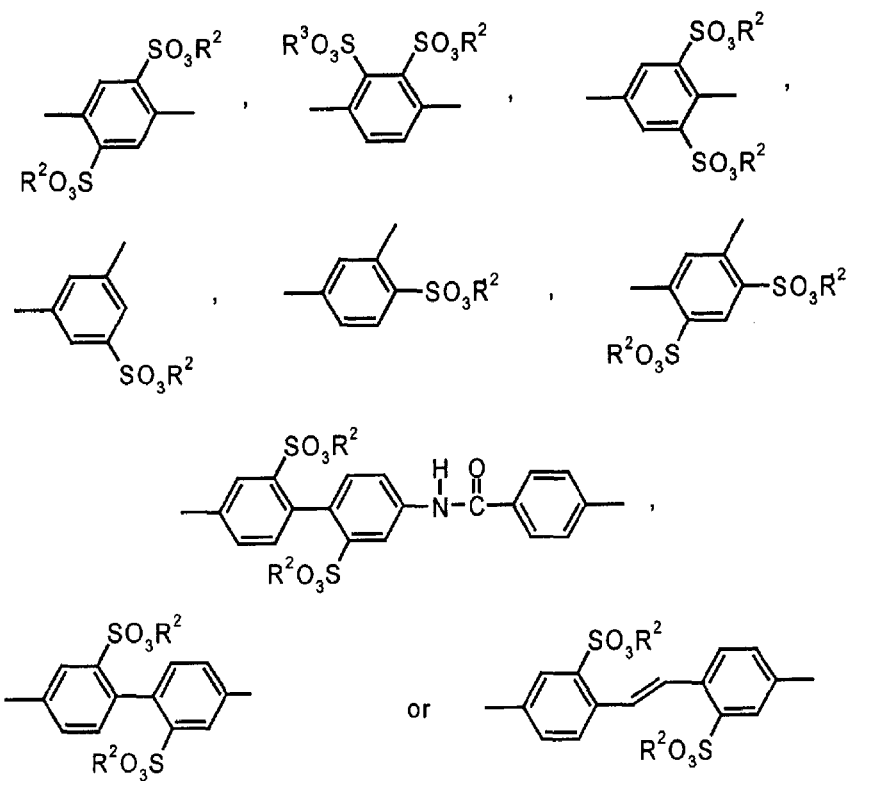

--

UNITED STATES PATENT AND TRADEMARK OFFICE
CERTIFICATE OF CORRECTION

PATENT NO.   : 6,086,864
DATED        : July 11, 2000
INVENTOR(S)  : Michael J. Mullins, William A. Fordyce, William J. Kruper, Norton P. Peet and Alan D. Cardin It is certified that error appears in the above-identified patent and that said Letters Patent is hereby corrected as shown below:

Column 20,
Line 7 reads "represents." and should read -- represents

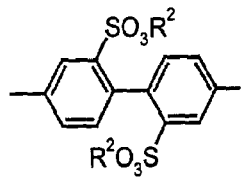 --

Signed and Sealed this

Second Day of July, 2002

Attest:

Attesting Officer

JAMES E. ROGAN
Director of the United States Patent and Trademark Office